United States Patent [19]

Patel

[11] Patent Number: 4,580,895

[45] Date of Patent: Apr. 8, 1986

[54] SAMPLE-SCANNING PHOTOMETER

[75] Inventor: Shailen S. Patel, Santa Monica, Calif.

[73] Assignee: Dynatech Laboratories, Incorporated, Alexandria, Va.

[21] Appl. No.: 546,451

[22] Filed: Oct. 28, 1983

[51] Int. Cl.[4] .......... G01N 33/48

[52] U.S. Cl. .......... 356/39; 356/422; 422/73

[58] Field of Search .......... 356/422, 39; 422/73

[56] References Cited

U.S. PATENT DOCUMENTS

| | | | |
|---|---|---|---|
| 4,312,728 | 1/1982 | Kamachi et al. | 356/39 X |
| 4,447,396 | 5/1984 | Kano | 356/442 X |
| 4,452,759 | 6/1984 | Takekawa | 356/39 X |

*Primary Examiner*—Bernard D. Pianalto

*Attorney, Agent, or Firm*—LeBlanc, Nolan, Shur & Nies

[57] ABSTRACT

An apparatus and method for reading agglutination tests and other procedures by scanning the contents of a microtest well or other sample-holding vessel to determine a certain charactersitic of the contents, such as the size of an agglutination button or other solid mass in the well.

13 Claims, 34 Drawing Figures

SAMPLE-SCANNING PHOTOMETER

FIELD OF INVENTION

This invention relates to photometers for measuring the light absorbance (also referred to as optical density) of samples of biological and other substances or materials.

BACKGROUND

Various photometers are commercially available for measuring the light absorbance of liquid samples in microtitration plates or other sample-holding vessels. One example of such equipment is the MR 600 Microplate Reader marketed by Dynatech Laboratories, Incorporated of Alexandria, Va.

Known photometers of the foregoing type do not read or measure the size or diameter of hemagglutination clots (also called hemagglutination buttons) or other masses of particulate or solid material in the bottom of the sample-holding well or other vessel. Furthermore, known photometers of the foregoing type do not indicate variations of optical density of the button or other solid mass throughout its cross section. As a result, known photometers of the foregoing type do not provide the measurements necessary for interpreting a variety of different assays such as hemagglutination tests, latex agglutination tests, and complement fixation tests.

Prior to this invention, the size and pattern of such hemagglutination buttons and other solid masses were customarily determined by visually inspecting the button or mass in the microtest well or other sample-holding vessel. Such visual inspection, however, is time consuming and subject to erroneous and nonuniform interpretation.

SUMMARY AND OBJECTS OF INVENTION

With the foregoing in mind, the general aim and purpose of this invention is to provide a novel photometer which measures the size of an agglutination button or other mass of solid or particulate material in the bottom of a microtest well or other sample-holding vessel. The photometer of this invention additionally generates the data for constructing a graph showing the optical density profile of the button or other mass across the well or other sample-holding vessel. Accordingly, the photometer of this invention is capable of reading and interpreting a variety of tests and other procedures such as agglutination assays (including hemagglutination and latex agglutination assays), complement fixation assays and colormetric procedures.

In the illustrated embodiment of this invention, the photometer's density-measuring light beam is stationary, and a microtitration plate or other sample-holding vessel is moved relative to the stationary beam between the beam's light source and a light-sensing photodetector, whereby the beam scans across each microtest well or other sample-holding vessel. The photodetector therefore produces an analog output signal which is generated during relative motion between the light beam and the sample-holding vessel to provide a travelling measurement which is indicative of the optical density of the button or other mass throughout the mass's entire cross section.

In the illustrated embodiment, the analog output signal of the photodetector is digitized and the digitized form of the photodetector's output signal is electrically processed to produce a read-out value which is indicative of the size or diameter of the button or other solid mass in the bottom of the well. Digitization of the photodetector's output signal may be accomplished by intermittently sampling the analog signal and converting the samples into digital signal form.

Rather than performing a continuous travelling measurement, the photometer's optical system (which includes the light source and photodetector) may be designed to provide discrete, spaced apart photometric measurements across the well or other sample-holding vessel. Such discrete measurements may either be of travelling type as described above or of the static type where relative motion between the sample-holding vessel and the light beam is temporarily interrupted while performing the measurement.

In addition to the foregoing, the subject invention involves a novel computer program-controlled procedure for moving of the microtitration plate or other sample-holding vessel and for generating a reading indicative of the size of the agglutination button or other mass in the bottom of the sample-holding vessel.

With the foregoing in mind, another object of this invention is to provide a novel photometer which reads hemagglutination and other agglutination type assays as well as other tests by photometrically scanning the contents of the microtest well or other sample-holding vessel.

Yet another object of this invention is to provide a novel program-controlled photometer.

Further objects of this invention will appear as th description proceeds in connection with the below-described drawings and the annexed claims.

DETAILED DESCRIPTION OF THE DRAWINGS

Figure 1:
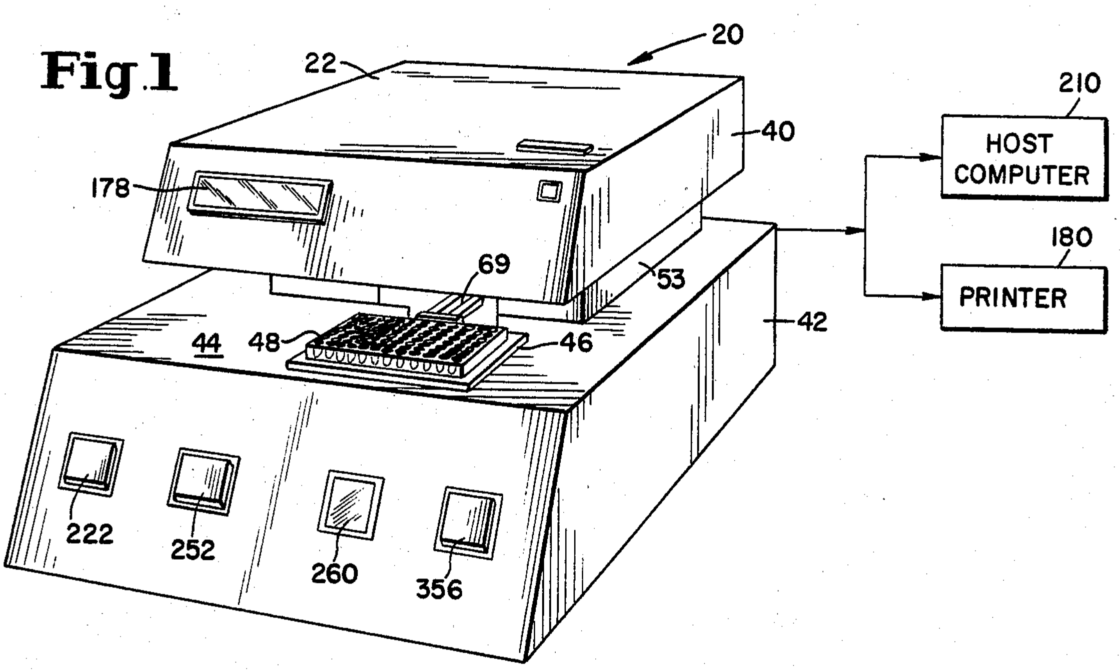
FIG. 1 is a perspective view of a photometer incorporating the principles of this invention.
Figure 2:
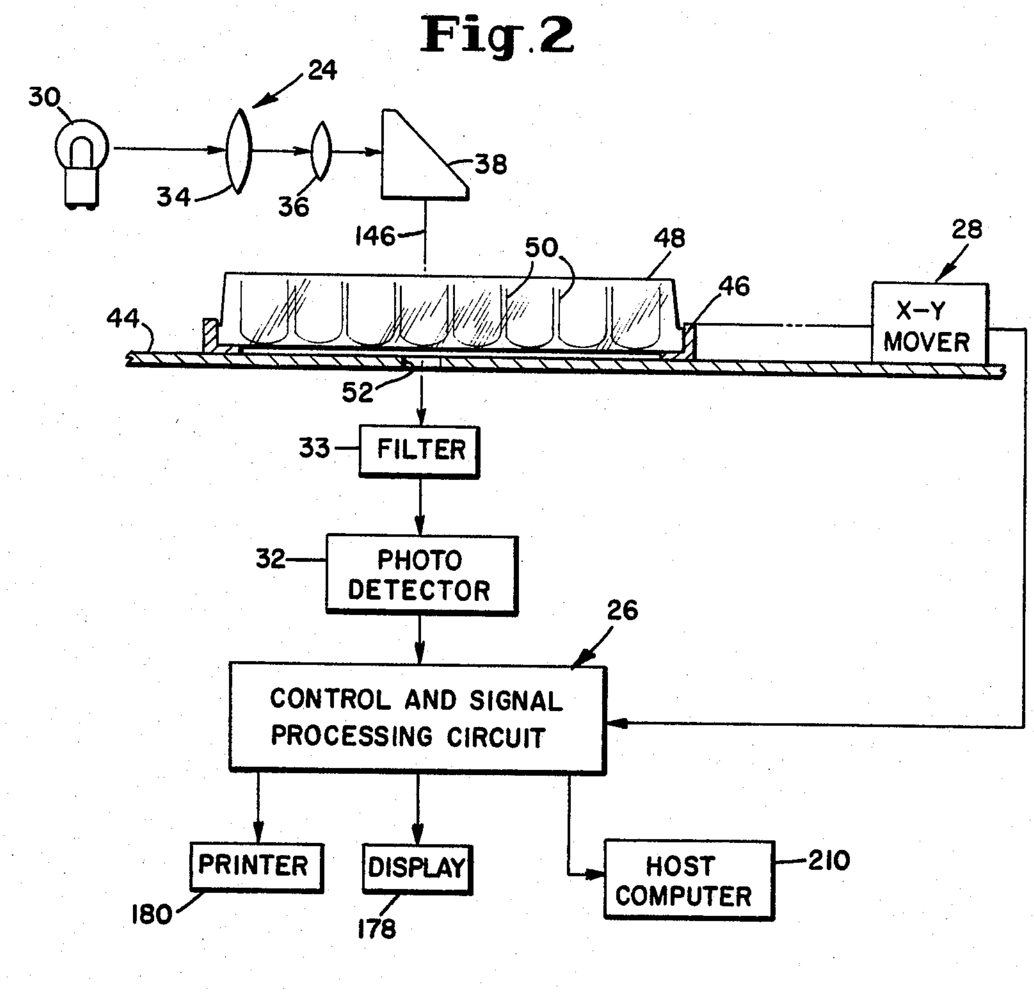
FIG. 2 is a schematic view of the functional components in the photometer of FIG. 1.

Referring to FIGS. 1 and 2, a photometer 20 incorporating the principles of this invention comprises a suitable casing 22 (FIG. 1) for housing the various components of the instrument, including an optical system 24 (FIG. 2), an electrical control and signal processing circuit 26 (FIG. 2), and an X-Y mover 28 (FIG. 2).

Optical system 24 may be of any suitable conventional type. In the illustrated embodiment it is the same as the optical system used in the previously identified MR 600 Microplate Reader.

As shown in FIG. 2, optical system 24 comprises a lamp 30 which operates as the optical system's light source, a photodetector 32 for detecting the light transmitted by lamp 30, a light filter 33, a prism 38, and suitable optics including a pair of lenses 34 and 36. Lamp 30 may be of any suitable type as a tungsten halogen lamp.

In the illustrated embodiment, lamp 30, lenses 34 and 36, and prism 38 are mounted in an upper casing portion 40, and photodetector 32 and filter 33 are mounted in a lower casing portion 42. Alternatively, lamp 30 and the optics may be mounted in the lower casing portion 42, and photodetector 32 may be mounted in the upper casing portion 40.

As best shown in FIG. 1, casing 22 has a support deck or table 44 for slidably supporting a rectangular holder 46. A microtitration plate 48 (also referred to as a microtest plate) is adapted to be seated in and supported by holder 46 for unitary displacement therewith. Deck 44 forms the top wall of the lower casing portion 42. Casing 22 may be the same as the one in the previously identified MR 600 Microplate Reader.

Figure 12:
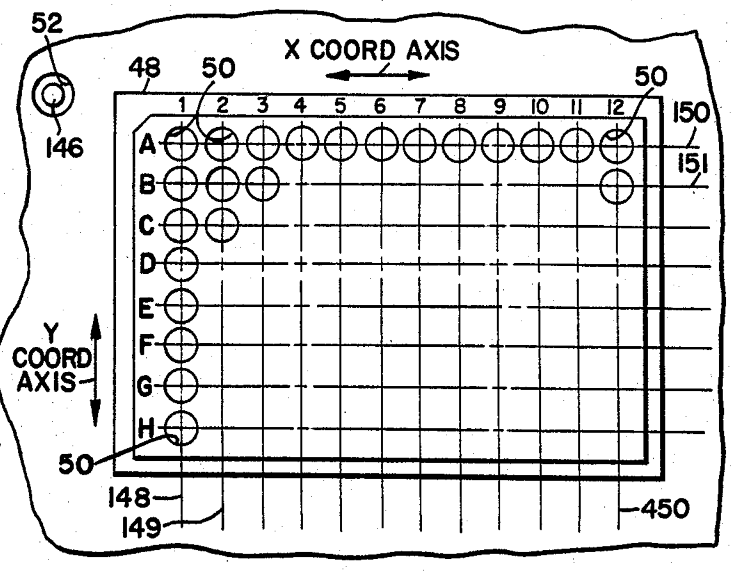
FIG. 12 is a plan view of the assembly of the microtitration plate and its holder at a home position relative to the X and Y coordinate axes.

Plate 48 may be of any suitable conventional clear plastic construction such as the one described in U.S. Pat. No. 3,356,462 which issued to N. M. Cooke et al on Dec. 5, 1967. This type of microtitration plate has an 8×12 array of 96 uniformly diametered, upwardly opening sample-holding wells 50. As shown in FIG. 12, wells 50 are uniformly spaced apart to form eight parallel spaced apart 12-well rows in one direction and twelve parallel spaced apart 8-well columns in a direction extending perpendicular to the above-mentioned rows. Microtitration plates of this type are customarily provided with alphabetic designations (A through H) for identifying the rows of wells and numerical designations (1 through 12) for identifying the columns of wells in the plate.

As will be described in detail shortly, the X-Y mover 28 is connected to holder 46 to move the assembly of holder 46 and plate 48 in a horizontal X-Y coordinate plane to successively bring wells 50 in a preselected order into axial alignment with an aperture 52 through deck 44. Light from lamp 32 is focused by lenses 34 and 36 to form a beam which is directed by prism 38 to pass downwardly through the top opening of the selected one of the wells 50 lying in alignment with aperture 52. Lenses 34 and 36 focus a beam of the lamp's light on the contents in the aligned well such that the beam passes downwardly through the well's open top, through aperture 52, and through filter 33 to photodetector 32. The output signal of photodetector 32 is a measure of the light absorbance and hence the optical density of the contents of well 50 at the point where the light beam passes through the well. In this embodiment only one filter of preselected wavelength is used for filtering the light passing through the sample in the well.

The particulars of the system thus far described are old and are the same as those in the previously identified MR 600 Microplate Reader. The X-Y mover 28 is also of conventional construction with exceptions which will be described below. Casing 22 has an intermediate portion 53 (see FIG. 1) which houses mover 28.

Figure 4:
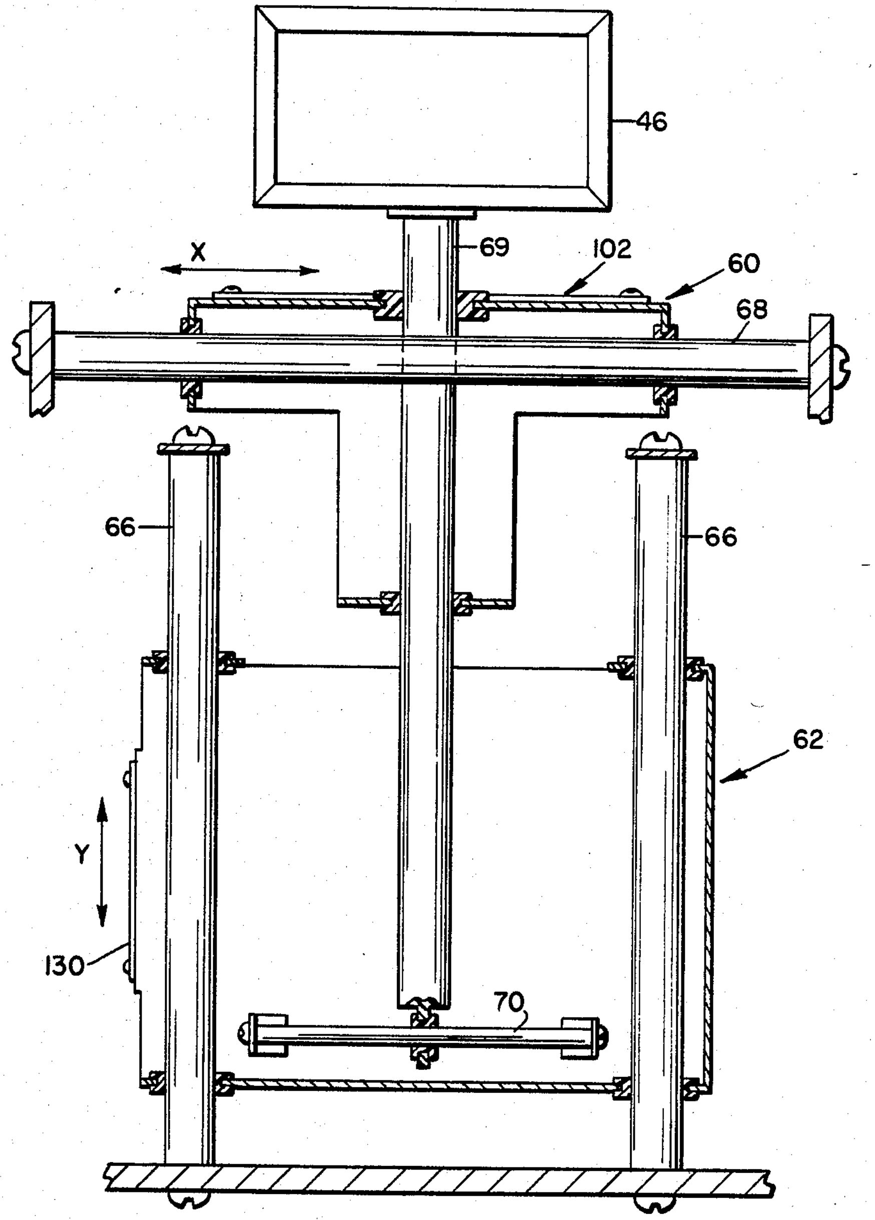
FIG. 4 is a partially schematic plan view of the X-Y mover shown in FIG. 2.
Figure 5:
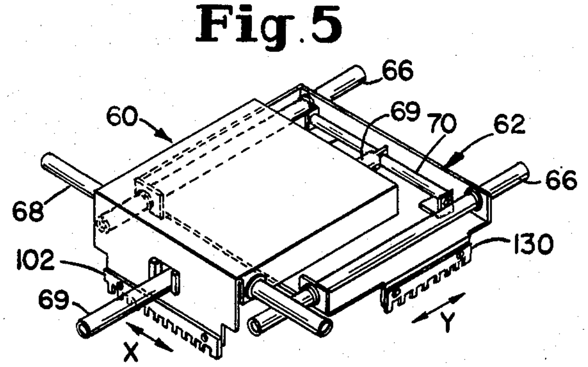
FIG. 5 is a fragmentary, perspective view of the X-Y mover shown in FIG. 4.

As shown in FIGS. 4 and 5, mover 28 comprises an X-motion carriage 60 and a Y-motion carriage 62. The Y carriage 62 is slidably mounted on a pair of fixed, parallel spaced apart rails 66 for reciprocal horizontal rectilinear movement parallel to the Y axis of the X-Y coordinate plane. The X carriage 60 is slidably mounted on a fixed guide rail 68 which is perpendicular to guide rails 66. A bar or member 69 is slidably mounted on X carriage 60, extends freely through an opening in casing portion 53, and is fixed at one end to holder 46. The other end member 69 slidably receives and is supported by a further guide rail 70, which is fixed on the Y carriage 62. Rail 70 is perpendicular to guide rails 66, and member 69 extends perpendicular to rail 70.

By the foregoing construction it will be appreciated that the assembly of X carriage 60 and member 69 is slidably mounted on the Y carriage 62 for reciprocal, rectilinear movement parallel to the X-coordinate axis, which is perpendicular to the Y direction of movement of Y carriage 62. It also will be appreciated that member 69 is axially displaceable with the Y carriage 62 parallel to the Y-coordinate axis and is laterally displaceable with the X carriage 60 parallel to the X-coordinate axis. The assembly of holder 46 and plate 48 is therefore displaceable in opposite directions parallel to the X-coordinate axis and is also displaceable in opposite directions parallel to the Y-coordinate axis. Plate 48 is positioned in such a manner that the alphabetically identified rows of wells 50 are parallel to the X-coordinate axis and the numerically identified columns of wells 50 are parallel to the Y-coordinate axis.

Figure 6:
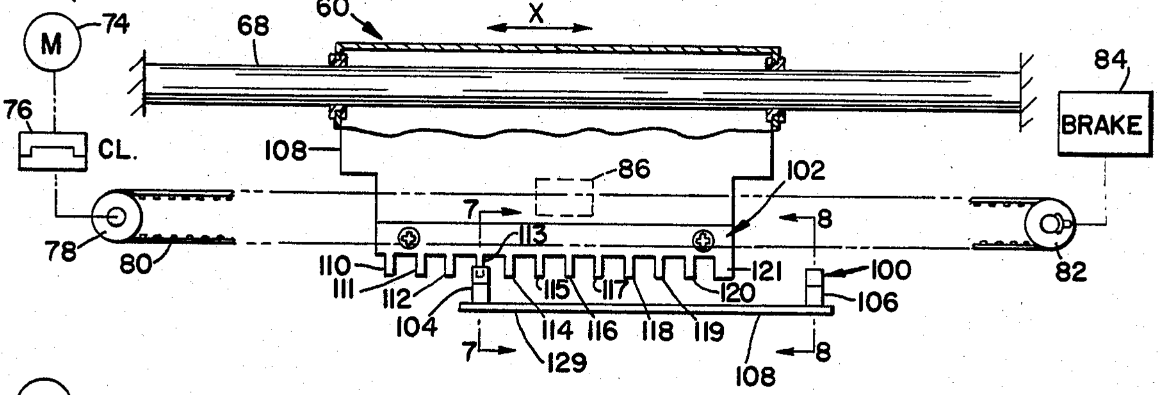
FIG. 6 is a partially schematic front elevation of the X-motion carriage and the motorized drive therefor.
Figure 9:
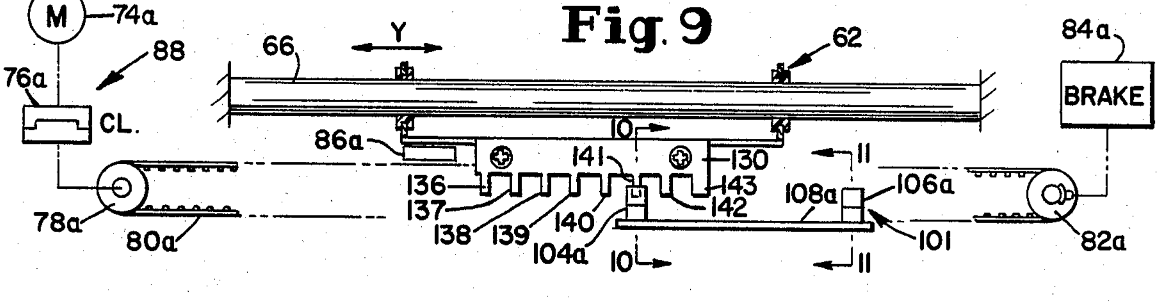
FIG. 9 is a partially schematic front elevation of the Y-motion carriage and the motorized drive therefor.

Referring to FIG. 6, a motorized drive 72 for driving the X carriage 60 in opposite directions parallel to the X-coordinate axis comprises a motor 74 which is drive connected by a clutch 76 to a toothed pulley 78. A drive belt 80 is trained around pulley 78 and another toothed pulley 82. Pulley 82 is connected to a brake 84.

The upper run of drive belt 80 is fixed to carriage 60 by any suitable means such as a bracket 86. On its inwardly facing side, drive belt 80 is provided with gear-like teeth which mesh with the teeth on pulleys 78 and 82 to prevent slippage of the drive belt.

Figure 7:
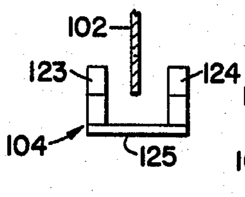
FIG. 7 is a section taken substantially along lines 8—8 of FIG. 6.

Referring to FIG. 7, a motorized drive 88 for driving the Y carriage 62 in opposite directions parallel to the Y-coordinate axis is the same as the X carriage drive 72. Accordingly, like reference numerals have been used to identify like parts of the two drives, except that the reference numerals used for the Y carriage drive have been suffixed by the letter "a" to distinguish them from the reference numerals used for the X carriage drive. In the case of the Y carriage drive 88, drive belt 80*a* is fixed by the bracket 86*a* to the Y carriage 62.

As shown in FIGS. 5, 6 and 7, a sensor assembly 100 is employed for sensing the position of plate 48 along the Y-coordinate axis, and a further sensor assembly 101 is employed for sensing the position of plate 48 along the Y-coordinate axis. Sensor assembly 100 may be of any suitable conventional type and is preferably the same as the one used in the previously identified MR 600 Microplate Reader.

As shown in FIGS. 5 and 6, sensor assembly 100 comprises a photobeam interrupt comb 102, a position sensor 104, and a home sensor 106. Comb 102 is fixed by any suitable means such as a bracket 108 to carriage 60. Comb 102 therefore moves with carriage 60 relative to sensors 104 and 106, which are stationary and which are of the photoelectric type.

As best shown in FIG. 6, comb 102 has a set of twelve parallel, uniformly spaced apart photobeam-interrupting teeth 110, 111, 112, 113, 114, 115, 116, 117, 118, 119, 120, and 121 which are arranged in a straight row extending parallel to the motion path of carriage 60 and hence to the X-coordinate axis. Tooth 121 at the right hand end of comb 102 (as viewed from FIG. 6) has a width which is greater than the uniform width of the other teeth of the comb.

Comb 102 and plate 48 are fixed against movement relative to one another along a path extending parallel to the X-coordinate axis. The uniform spacing between teeth 110–121 is equal to the uniform spacing between the columns of wells 50 in plate 48.

As best shown in FIG. 7, sensor 104 comprises a lamp or other suitable light source 123, a photodetector 124 and a U-shaped holder 125 which mounts light source 123 and photodetector 124. Photodetector 124 is positioned to detect the light transmitted by light source 123. Comb 102 moves with carriage 60 along a path where its teeth 110-121 pass between light source 123 and photodetector 124 at right angles to the light beam to thus interrupt the light beam generated by light source 123.

Figure 8:
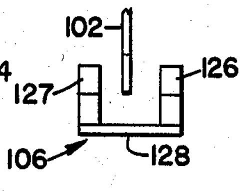
FIG. 8 is a section taken substantially along lines 9—9 of FIG. 6.

As best shown in FIG. 8, sensor 106 also comprises a lamp or other suitable light source 126, a photodetector 127, and a U-shaped holder 128 which mounts light source 126 and photodetector 127. The light beam transmitted by light source 126 is detected by photodetector 127. Holders 116 and 122 are fixed against movement and may be mounted on any suitable part or member which is indicated at 129 in FIG. 4

The motion path of comb 102 extends between light source 126 and photodetector 127 such that tooth 121 at the right hand end of comb 102 (as viewed from FIG. 6) interrupts the light beam transmitted by light source 126 upon movement of carriage 60 to its home position.

Referring to FIGS. 5, 10, 11 and 12, sensor assembly 101 also comprises a photobeam interrupt comb 130, a position sensor 104*a* and a home sensor 106*a*. Sensors 104*a* and 106*a* are the same as sensors 104 and 106, respectively. Accordingly, like reference numerals have been applied to designate corresponding components of the two sets of sensors except that the reference numerals used for sensors 104*a* and 106*a* have been suffixed by the letter "a" to distinguish them from the reference numerals used for sensors 104 and 106.

Figure 10:
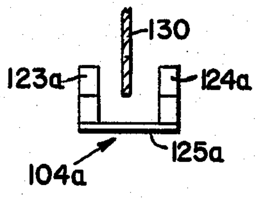
FIG. 10 is a section taken substantially along lines 10—10 of FIG. 9.
Figure 11:
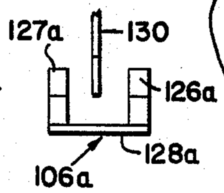
FIG. 11 is a section taken substantially along lines 11—11 of FIG. 9.

As best shown in FIG. 10, comb 130 is similar to comb 102, but instead of having twelve teeth, it has a set of just eight parallel, uniformly spaced apart photobeam-interrupting teeth 136, 137, 138, 139, 140, 141, 142 and 143 which are arranged in a straight row extending parallel to the motion path of carriage 62 and hence to the Y-coordinate axis. The uniform spacing between teeth 136 is equal to the uniform spacing between the rows A–H of wells 50 in plate 48. Comb 130 and plate 48 are fixed against relative movement to one another along a path extending parallel to the Y-coordinate axis.

Comb 130 moves with the X carriage 62 along a path where its teeth 136–143 pass between light source 123*a* and photodetector 124*a* at right angles to the light source's beam to thus interrupt the light beam generated by light source 123*a*. The motion path of comb 130 also extends between light source 126*a* and photodetector 127*a* such that tooth 143 interrupts the light beam transmitted by light source 126*a* upon movement of carriage 62 to its home position.

The light beams generated by light sources 123 and 126 are parallel and are spaced apart by a distance which is greater by a preselected length than the spacing between oppositely facing edges of the comb's endmost teeth 110 and 121. Similarly, the light beams transmitted by light sources 123*a* and 126*a* are parallel and are spaced apart by a distance which is greater by a preselected length than the spacing between oppositely facing edges of the comb's endmost teeth 136 and 143. Because of this arrangement, the home position of the assembly of holder 46 and plate 48 will be spaced from the photometer's vertical light beam 146 in the plane where it passes centrally through aperture 52 as shown in FIG. 12.

When the X carriage 60 is advanced away from its home position to a position where tooth 110 interrupts the beam from light source 123, plate 48 will be at a position where a column line 148 (FIG. 12) normally intersecting the longitudinal axes of wells 50 in column 1 perpendicularly intersects the longitudinal photometer's light beam 146. When carriage 60 is displaced to its next position where tooth 111 interrupts the light beam from light source 123 plate 48 will be at a position where a column line 149 perpendicularly intersecting the longitudinal axes of the wells in column 2 perpendicularly intersects the photometer's light beam 146. For succeeding X carriage positions at which the beam from light source 123 is interrupted by teeth 112–121, plate 48 will be at locations where corresponding column lines for the plate's columns 3–12 intersect light beam 146.

The position of comb 130 relative to plate 48 differs from the arrangement in the previously identified MR 600 Microplate Reader and is such that when the Y carriage 62 is displaced away from its home position to a position where tooth 136 interrupts the light beam from light source 123*a*, the photometer's light beam 146 will be perpendicularly intersected by a row line 150 (FIG. 12) passing through the wells in row A of plate 48 immediately adjacent to the wells' leading edges relative to light beam 146. Line 150 is thus offset from the centers of the wells. When the Y carriage 62 is advanced to a position where tooth 137 interrupts the beam from light source 123*a*, plate 48 will be at a position where light beam 146 is intersected by another row line 151 passing through the wells in row B immediately adjacent to the wells' leading edges relative to light beam 46, similar to line 150. For succeeding Y carriage positions where the beam from light source **123*a* is interrupted by teeth 138–143, plate 48 will be at locations where corresponding row lines for the plate's rows C-H intersect light beam 46**. The row lines mentioned above are parallel to one another and are perpendicular to the previously mentioned column lines.

As will be described in greater detail shortly, movement of carriages 60 and 62 is programmed in such a way that the carriages are first advanced from their home positions to positions where tooth 110 interrupts the beam from light source 123 and tooth 136 interrupts the light beam from light source **123*a*, thus locating plate 48 at a position where the photometer's light beam 146 passes through the intersection of lines 148 and 150 and hence through the A1 well in plate 48 immediately adjacent to the well's leading edge where it is substantially offset from the well's centerline. At this stage of the operation the movement of the X carriage is halted while continuing the movement of the Y carriage 62 away from its home position, whereby beam 146 traverses along line 148**.

The Y-axis movement along line 148 continues until plate 48 reaches a point adjacent to the trailing edge of the H1 well. Carriage 62 then returns to its home position, and carriage 60 is advanced to its next interrupt position where tooth 111 interrupts the beam from light source 123. At this stage, movement of the X carriage 60 is again halted while continuing the movement of the Y carriage 62, whereby the photometer's light 146 advances or scans along line 149 to a point adjacent to the trailing edge of the H2 well.

The foregoing scanning operation is repeated column by column for each of the remaining columns 3-12 in plate 48. After the plate's wells in column 12 are scanned to complete the scanning operation, carriages 60 and 62 are returned to their home positions.

From the foregoing it will be appreciated that the photodetector's analog output signal (which is a measure of the intensity of the photometer's light beam and hence the extent to which light has been absorbed) represents a continuous, travelling measurement of the sum of two optical densities, the first being the optical density of the substance in each well diametrically across each entire well, and the second being the optical density of the well's bottom.

Figure 3:
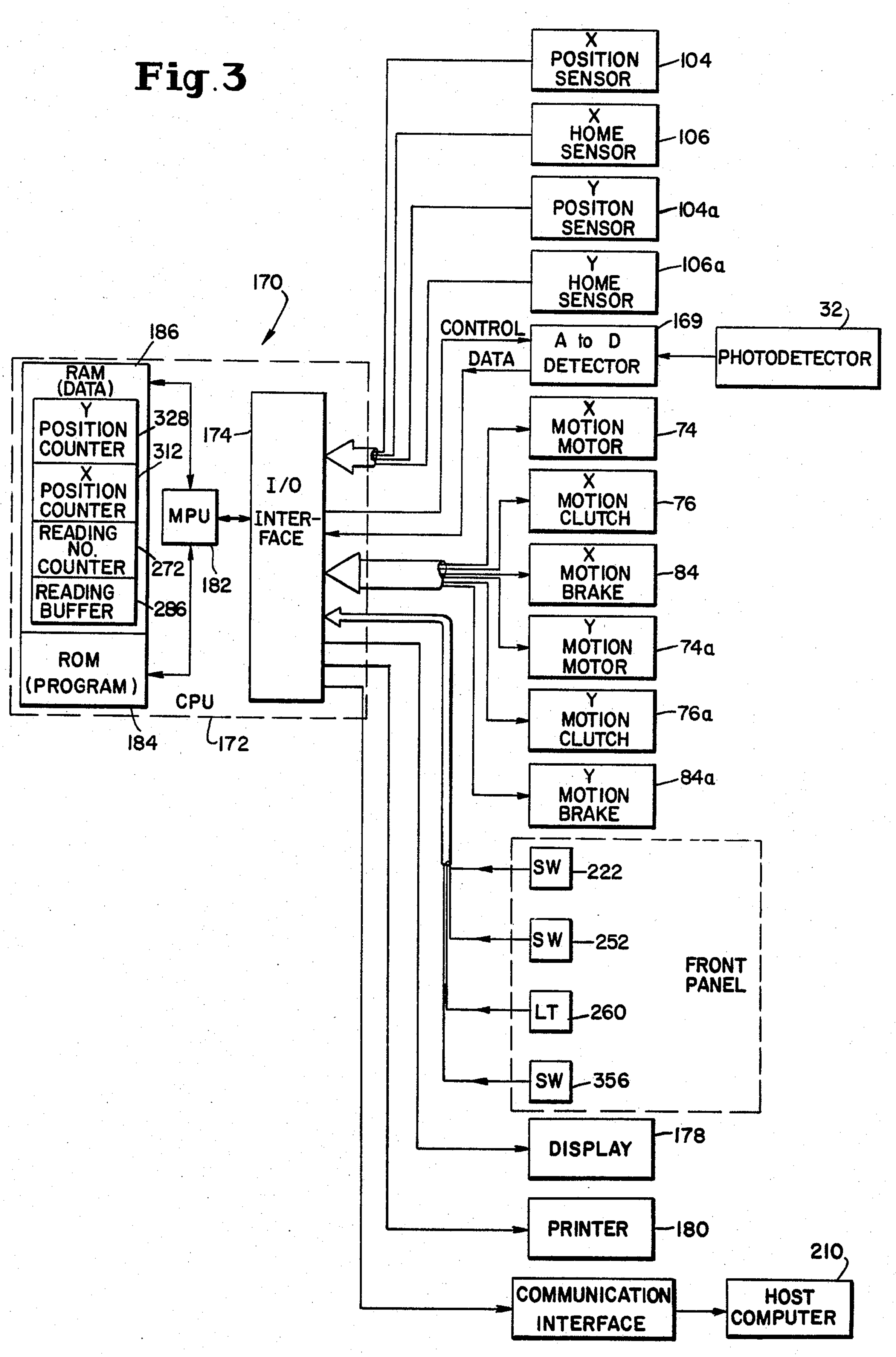
FIG. 3 is a schematic block diagram of the control and signal processing circuit shown in FIG. 2.

Referring to FIG. 3, the analog output signal of photodetector 32 is periodically sampled by an analog-to-digital converter 169 as the photometer's light beam diametrically traverses each of the wells 50 in plate 48 to digitize the photodetector's analog output for each of the plate's wells. Any suitable number of signal samples may be taken of the photodetector's analog output for each of the wells 50.

Figure 13:
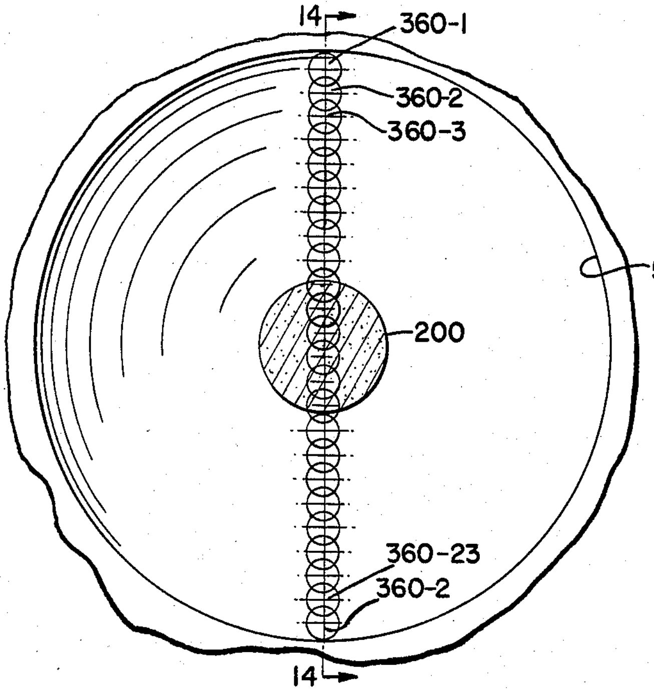
FIG. 13 is an enlarged fragmentary plan view of one of the wells of the microtest plate shown in FIGS. 1 and 12.
Figure 14:
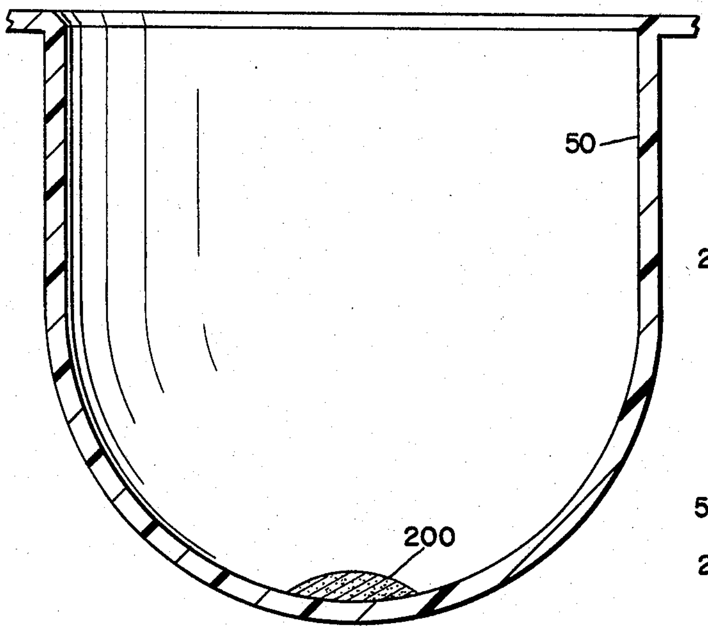
FIG. 14 is a section taken substantially along lines 14—14 of FIG. 13.
Figure 15A:
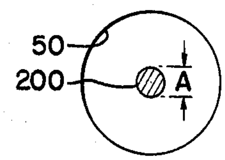
FIGS. 15A, 16A, 17A, 18A and 19A are fragmentary plan views of the wells similar to FIG. 13 and showing various sizes of hemagglutination buttons.
Figure 15B:
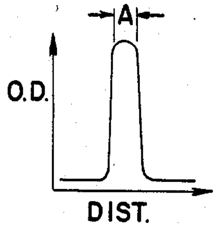
FIGS. 15B, 16B, 17B, 18B and 19B are optical density profile graphs of the buttons shown in FIGS. 15A–19A, respectively.
Figure 16A:
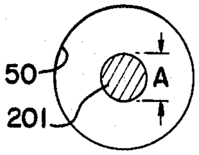
Figure 16B:
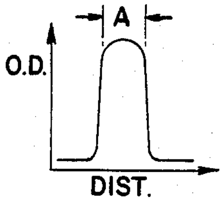
Figure 17A:
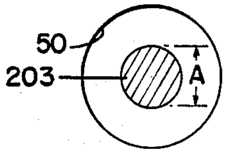
Figure 17B:
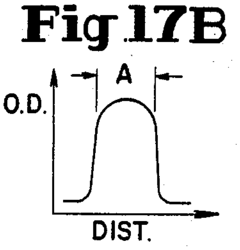
Figure 18A:
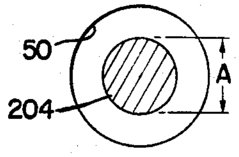
Figure 18B:
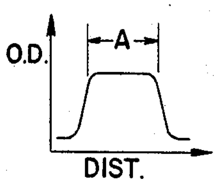
Figure 19A:
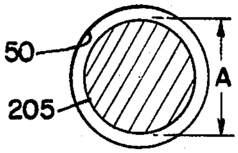
Figure 19B:
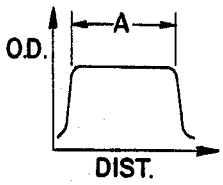

In the illustrated embodiment, twenty-four signal samples of the photodetector's analog output are taken periodically such that the samples are uniformly spaced apart diametrically across each well as shown in FIG. 13. Because the Y carriage 62 is advanced at a uniform speed, the twenty-four samples of the photodetector's analog output signal for each well will be uniformly spaced apart as illustrated in FIG. 13. The signal samples are each converted by converter 169 into digital signal form, that is a plural bit word. Sampling of the photodetector's analog output signal is commenced for each of the wells 50 in plate 48 in a manner described below.

The digital optical density readings for each of the wells 50 are processed by a microcomputer 170 in circuit 26 to produce and to read out a value of the size or diameter of any agglutination button or other solid mass in the bottom of the well. For a hemagglutination inhibition assay, the diameter of the hemagglutination button may be indicated by a numerical value on a scale of 1 through 5.5 where the numerical value 1 represents a strong negative reaction, the numerical value 2 represents a weak negative reaction, the numerical value 3 represents an intermediate reaction, the numerical value 4 represents a weak positive reaction, and the numerical value 5 represents a strong positive reaction.

Referring to FIGS. 15A–19A and 15B–19B a strong hemagglutination inhibition reaction results in a small, tight hemagglutination button 200. As the reaction becomes less negative and hence more positive the button size increases, and the button becomes less compact or looser as indicated by the button sizes 201, 202, 203 and 204 in FIGS. 16A–19A, respectively. It will be appreciated that any other suitable numerical values may be used to indicate the button size.

In addition to reading the size of a hemagglutination button, the digitized optical density measurements for each well may be transmitted to a host computer 210 for plotting a graph showing the optical density pattern or profile of the button or other solid mass in the cross-section, as illustrated, for example, in FIGS. 15B–19B.

It will be appreciated that the foregoing hemagglutination inhibition assay readings are but one example of the measurements and readings which the photometer of this invention is capable of performing. In general, the photometer of this invention is capable of measuring and reading out the size of any particulate or other solid mass in the bottom of a microtest well or other sample-holding vessel. The digitized measurements for each sample may also be transmitted to a host computer for plotting the optical density profile of such mass in cross-section. Such plots have particular value for recognizing various patterns of the masses the optical density.

As shown in FIG. 3, microcomputer 170 comprises a central processing unit 172 which is connected through an input/output interface 174 to the input and output devices in the system. The input devices include sensors **104, 106, 104*a*, and 106*a* and converter 169. The output devices include motors 74 and 74*a*, clutches 76 and 76*a*, brakes 84 and 84*a*, and one or more suitable read-out devices such as an LED display module 178 and a printer 180. Central processing unit 172 inclues a microprocessor 182, or other suitable processor, a read only memory (ROM) 184 for electrically storing the computer's program, and a random access memory (RAM) 186 for storing data and other information. The program in ROM 184 provides the instructions for automatically operating the photometer 20 and for generating the readings read out on display 178 and/or printer 180. The flow chart for the resident program is shown in FIGS. 20–29**.

Figure 20:
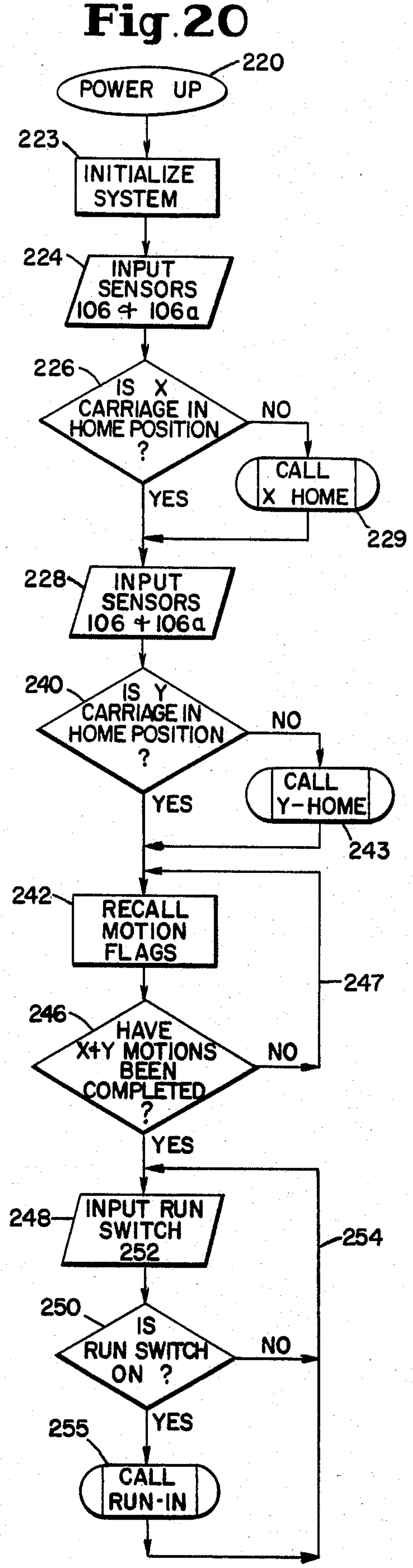
FIG. 20 is a flow chart of the computer program according to one embodiment of this invention.

Referring to FIG. 20, the program commences with a start or power-up step 200 in which power is applied to the photometer by operating an on/off power switch 222 on a front panel of casing 22. The power-up step 220 is followed by an initialization step 223 which may be the same as the one used in the previously identified MR 600 Microplate Reader for initializing various pointers and counters in the CPU, for clearing internal processor registers and conducting other housekeeping operations such as disabling all interrupts, turning off motors 74 and 74a, disengaging clutches 76 and 76a and releasing brakes 84 and 84a.

Following step 223, input step 224 is entered to check or interrogate sensors 106 and 106a. If carriage 60 is in its home position, sensor 106 will transmit an interrupt signal to microprocessor 182. If carriage 62 is in its home position, sensor 106a will transmit a similar interrput signal to microprocessor 182. Sensor 106 generates its interrupt signal when tooth 121 interrupts the light beam from source 126, and sensor 106a generates its interrupt signal beam when tooth 143 interrupts the light beam from source 126a.

Following input step 224, a decision step 226 is entered to look at the signal from sensor 106 to determine whether the X carriage 60 is in its home position. If the decision is affirmative, a second sensor input step 228 is entered. If the decision at step 226 is negative, step 229 is entered to call an X home subroutine 230 (FIG. 21) to commence movement of carriage 60 towards its home position.

Figure 21:
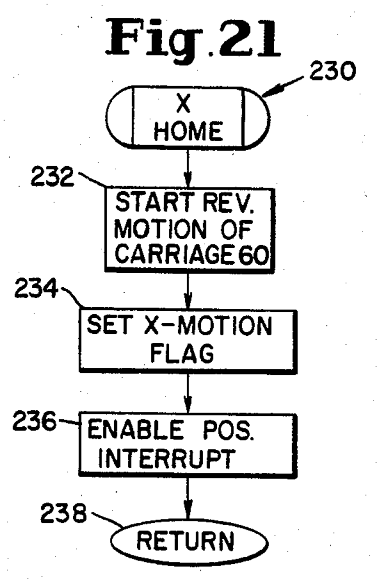
FIG. 21 is a flow chart of the X home subroutine.

Referring to FIG. 21, the X home subroutine commences with a start reverse step 232 for carriage 60. In this step, brake 84 is released, clutch 76 is engaged and motor 74 is actuated in the reverse direction.

Upon commencing motion of the X carriage 60, step 234 is entered to set or turn on an X-motion flag in RAM 186. The X-motion flag is simply a coded plural bit word which is placed in RAM 186 to inform microprocessor 182 that carriage 60 is in motion. Thereafter, an enable position interrupt step 236 is entered. In this step, microprocessor 182 is conditioned to recognize an interrupt signal from sensor 106 and, upon reception of the interrupt signal, to execute a position interrupt service or routine 237 (FIG. 25), which will be explained in detail later on. As explained above, each of the sensors 104, 106, 104a and 106a generates its interrupt signal when its light beam is interrupted. Upon commencing homeward movement of the X carriage 60, execution of the X home subroutine 230 is completed, and operation is returned at 238 (FIG. 21) to the main program (FIG. 20) at step 228.

Step 228 is the same as step 224 for checking or interrogating the signal status of sensors 106 and 106a. Upon inputting the signals from sensors 106 and 106a, a further decision step 240 is entered. Based on the signals supplied at step 228, step 240 determines whether or not the Y carriage 62 is at its home position. If the decision for step 240 is affirmative (signifying that carriage 62 is at its home position) a motion flag recall step 242 is entered. If carriage 62 is not at its home position, step 243 is entered to call a Y home subroutine 224 for commencing reverse motion of carriage 62.

Figure 22:
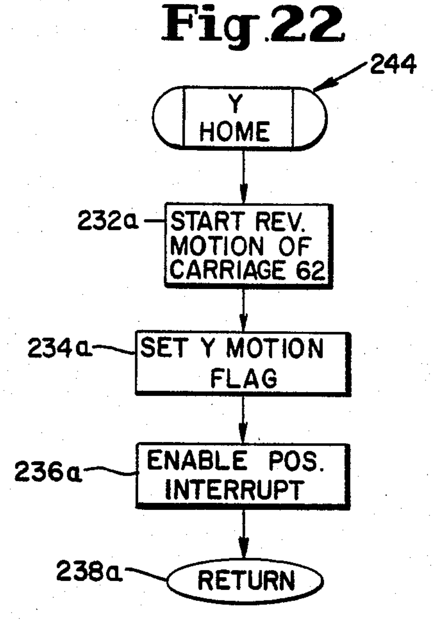
FIG. 22 is a flow chart of the Y home subroutine.

As shown in FIG. 22, the steps in subroutine 244 correspond to those in the X home subroutine 220. Accordingly like reference numerals have been applied to designate similar or corresponding steps in the two subroutines except that the reference numerals used to designate the steps in subroutine 244 have been suffixed by the letter "a" to distinguish them from the reference numerals used for the steps in subroutine 220.

The steps in subroutine 244 are applicable to the Y carriage 62 and its home sensor 106a. Thus, at step 232a, clutch 76a is engaged, brake 84a is released and motor 74a is actuated in the reverse direction to commence motion of carriage 62 towards its home position. At the flag-setting step 234a a Y-motion flag (a plural bit word in RAM 186) is set or turned on to inform microprocessor 182 that carriage 62 is in motion. At the enable interrupt step 236a, microprocessor 182 is conditioned to recognize an interrupt signal from sensor 106a and to execute the interrupt routine 237.

Upon executing the Y home subroutine 244, operation is returned at 238a (FIG. 22) to the main program at step 242. At this stage, therefore, both of the carriages 60 and 62 are travelling towards their respective home positions.

When the X carriage 60 arrives at its home position, it causes sensor 106 to transmit an interrupt signal to microprocessor 182. Alternatively, carriage 62 may arrive at its home position first, causing sensor 106a to transmit its interrupt signal. In either case, microprocessor 182 will now proceed to execute the interrupt routine 237.

Figure 25:
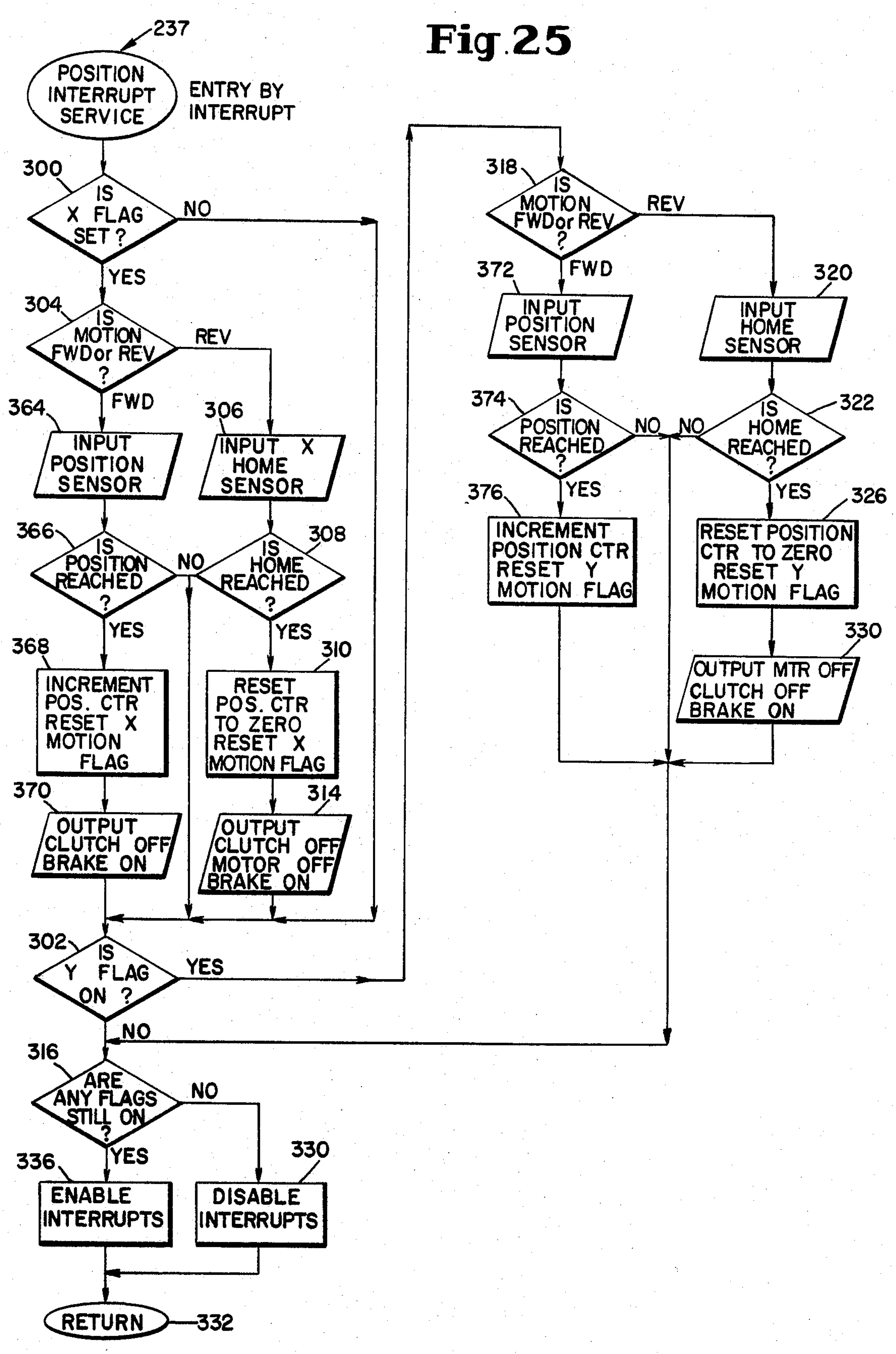
FIG. 25 is a flow chart of the interrupt routine.

As shown in FIG. 25, the interrupt service or routine 237 commences with a decision step 300 to determine if the X-motion flag is set. If the decision at step 300 is affirmative another decision step at 304 is entered to determine if the X carriage motion is forward or reverse. At this point of the operation, the motion will be in the reverse to proceed to an input step 306 where the signal from home sensor 106 is interrogated.

Following the input step 306, another decision step 308 is entered to determine if carriage 60 has arrived at its home position by examining the signal from input step 306. If the decision at step 308 is negative, the operation proceeds to decision step 302. If, on the other hand, the decision at step 308 is affirmative, a reset step 310 is entered to reset an X position counter 312 (see FIG. 3) to zero and to reset or turn off the X-motion flag. An output step 314 is then entered to disengage clutch 76, turn off motor 74 and apply brake 84, thus halting motion of the X carriage 60 at its home position.

From step 314, decision step 302 is entered to determine if the Y-motion flag is set or on. If it is not, the operation proceeds to a further decision step 316. If it is, the operation proceeds to yet another decision step 318 to determine whether the motion of the Y carriage 62 is forward or reverse. In this instance, the motion of carriage 62 will be in the reverse, thus entering an input step 320 where the signal from sensor 106a is interrogated. This signal is operated on at a following decision step 322. If the signal from sensor 106a indicates that carriage 62 is in its home position, a reset step 326 is entered to reset the Y-motion position counter 328 (FIG. 3) to zero and to reset or turn off the Y-motion flag. Each of the position counters 312 and 328 is a block of memory locations in RAM 186 which are incremented during motion of their respective carriages to indicate the X, Y coordinate positions of plate 48. The technique for providing such counters is conventional.

Upon exiting from step 326, an output step 330 is entered to turn off motor 74a, to disengage clutch 76a and to apply brake 84a, thus stopping the Y carriage 62 at its home position. At this stage, both carriages 60 and 62 will be at their home positions.

Following the output step 300, decision step 316 is entered to determine if the X-motion flag and/or Y-motion flags are still on. If the decision at step 316 is negative, an interrput disable step 330 is entered to disable the interrupt status in microprocessor 182, thus completing the execution of the position interrupt service 237 and returning at 332 in the main program. If either or both of the X-motion and Y-motion flags are still on, the decision at step 316 will be affirmative to enter another enable interrupt step 336 which again conditions microprocessor 182 to recognize the interrupt signals from sensors 106 and 106*a* and to thus place the processor in a condition for re-executing the interrupt routine 237.

The main program (FIG. 20) proceeds with the recall step 242 and a decision step 246. Step 242 recalls the X-motion and Y-motion flag conditions in memory 186. Based on the conditions of the flags, decision step 246 determines whether the motion of carriages 60 and 62 have been completed. If either or both of the flags are in their set conditions(to indicate that either or both of the carriages 60 and 62 are still in motion), the decision at step 246 will be negative to enter a waiting loop 247, thus looping the operation back to step 242. The waiting loop will continue until the X-motion and Y-motion flags are reset, at which time the decision at step 246 becomes affirmative, causing the operation to advance to an input step 248 to interrogate the condition or status of an on/off run switch 252 (see FIG. 1). Switch 252 is located on the front panel of photometer 20.

If run switch 252 is not on, the decision at decision step 250 is negative to enter a waiting loop 254. When run switch 252 is manually turned on by the operator an affirmative decision occurs at decision step 250, the waiting loop 254 is exited, and step 255 is entered to call a run-in subroutine 256 (FIG. 23).

Figure 23:
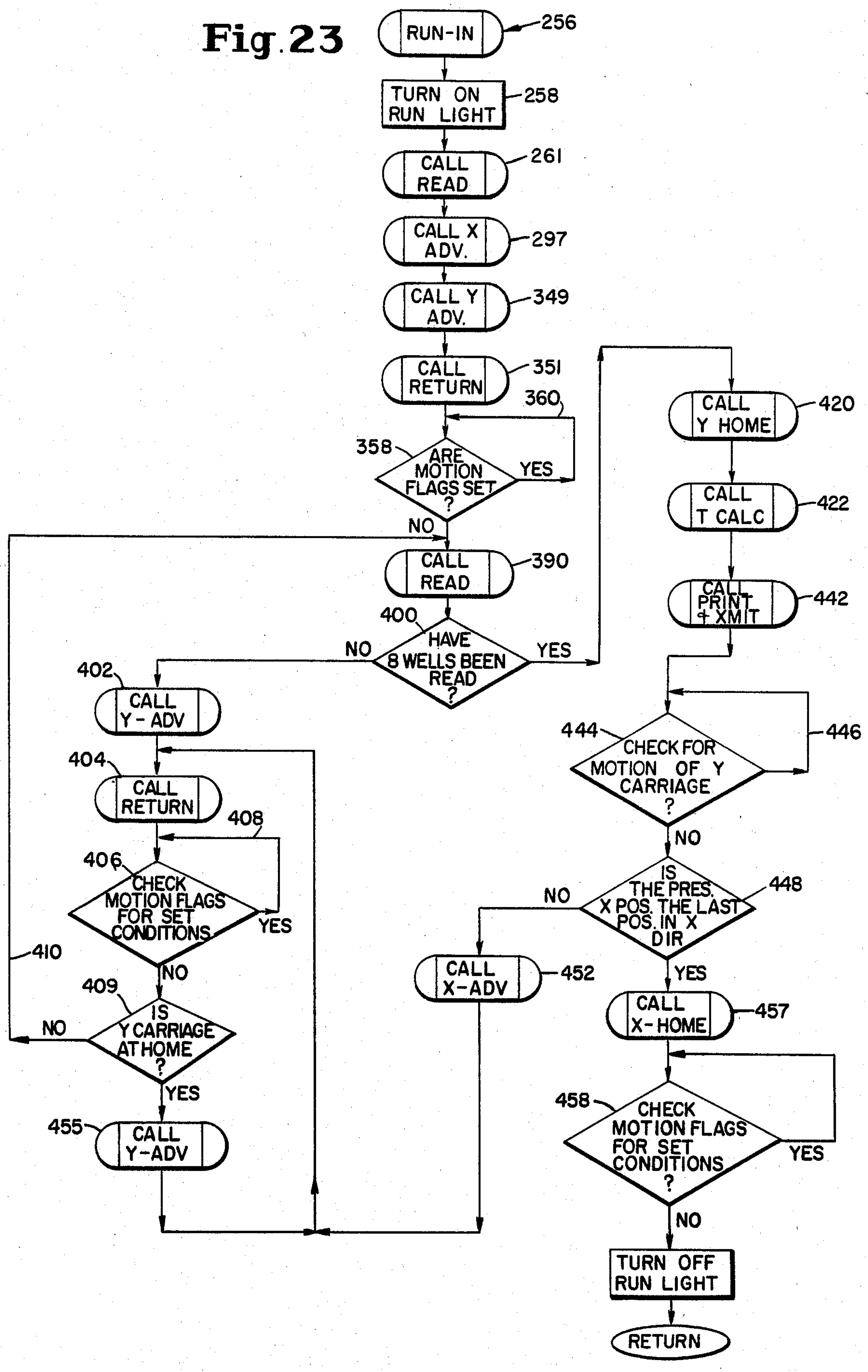
FIG. 23 is a flow chart of the run-in subroutine.
Figure 24:
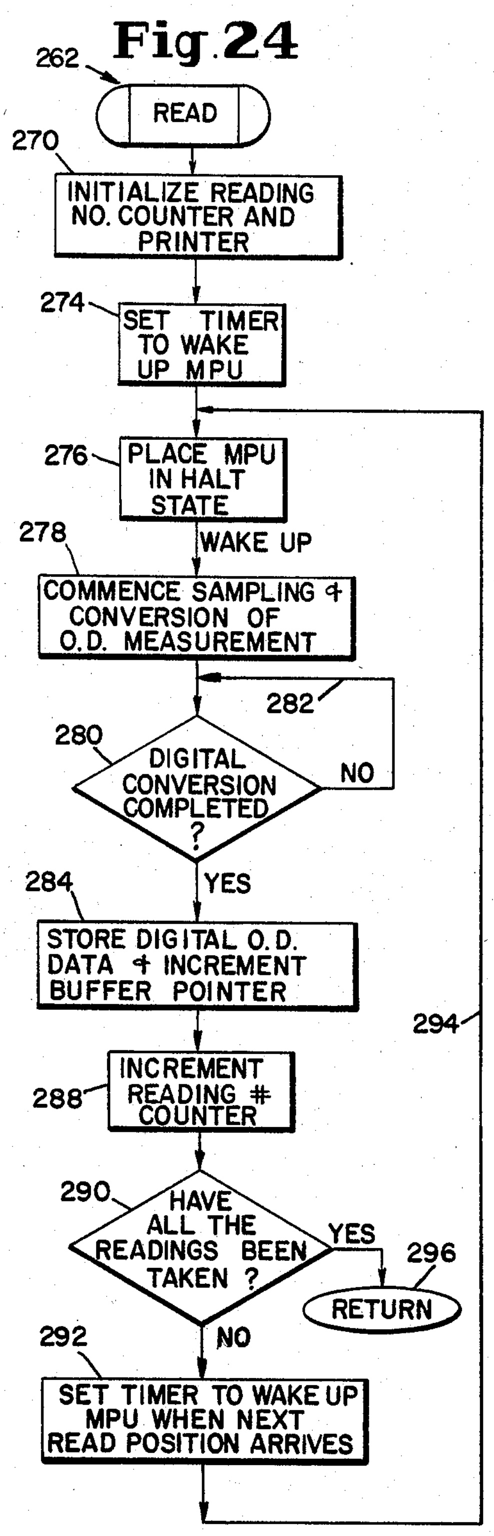
FIG. 24 is a flow chart of the read subroutine.

Referring to FIG. 23, subroutine 256 commences with a step 258 which commands the microprocessor 182 to turn on a run light 260 (see FIG. 1) on the front panel of the photometer. Following step 258, a step 261 is entered to call a read subroutine 260 (FIG. 24). The read subroutine instructs microprocessor 182 to operate the analog-to-digital converter 169 in such a manner that the converter periodically samples the analog output of photodetector 32, thus producing a preselected number of digitized optical density readings of the photodetector's analog output. In the illustrated embodiment, converter 169 operates to take twenty-four readings of the photodetector's output for each execution of subroutine 262. The twenty-four readings are taken at a constant frequency, whereby the time durations between the readings are equal.

When the read subroutine 262 is first executed, carriages 60 and 62 will be at their home positions, thus locating plate 48 at a position where it is spaced from the path of the photometer's light beam 146. Beam 146 therefore passes only through the air, and the twenty-four reading of the photodetector's analog output therefore represent the optical density of the ambient condition in which the photometer is operating. These twenty-four readings are averaged to produce what is customarily referred to as an "air blank" reference which is stored in RAM 186. At a later stage in the operation, the air blank reference is subtracted from the optical density reading obtained for each well 50 to correct for the effect of ambient air on the optical density readings.

Referring to FIG. 24, the read subroutine 262 commences with a step 270 which initializes a reading number counter 272 (see FIG. 3) and a pointer (not shown) for counter 272. Counter 272 is a block of RAM memory locations in which a pointer is incremented by microprocessor 182 to keep a count of the number of readings or samples taken by converter 169 for each sampling operation. Such a counting technique is conventional. Counter 272 also provides the addresses at which the digital output signals of converter 169 are stored in RAM 186.

Following step 270 in subroutine 262 (FIG. 24), a set time step 274 is entered. In this step a CPU timer (not shown) is conditioned to set the "wake-up" time for microprocessor 182 preparatory to a following step 276 in which microprocessor 182 is placed in its halt or sleep state.

In step 276, microprocessor 182 is placed in its halt step and when the CPU timer times out, the microprocessor is placed in its active or wake-up state to enter a signal sampling and conversion step 278 in which converter 169 is operated to sample the analog output of photodetector 32 and to convert the sample into a plural digital word for storage in RAM 186. The constant signal sampling frequency is such that the time required for taking the twenty-four digital readings is just slightly shorter than the time taken by carriage 62 to travel the diameter of the microtest well 50, thus ensuring that twenty-four digital optical density readings will be taken at each well 50.

Following step 278, a decision step 280 is entered to determine if converter 169 has completed the conversion of the analog sample presently being taken. If the decision is negative, a waiting loop 282 is entered until the digital conversion is completed, at which time the decision becomes affirmative to advance to a data storage step 284. At step 284, the digitized optical density reading is stored in a reader buffer portion 286 (FIG. 3) of RAM 186 at an address location indicated by a reader buffer pointer (not shown). The pointer for reading buffer 286 is thereupon incremented or advanced to the next address location in the reader buffer.

Following step 284, a counter incrementing step 288 is entered in which counter 272 is incremented so that it will have a count of the number of digitized optical density measurements thus far stored in buffer 286 for a given execution of subroutine 262.

Figure 26:
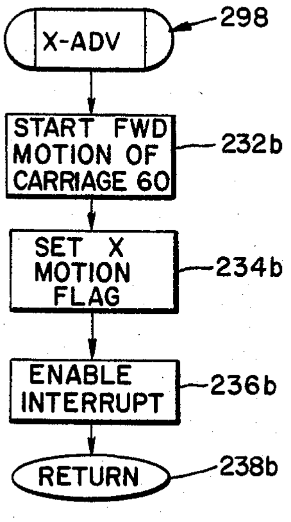
FIG. 26 is a flow chart of the X advance subroutine.

Thereafter a decision step 290 is entered to determine if all twenty-four digital optical density readings have been taken for a given execution of subroutine 262. If the decision for step 290 is negative, the operation proceeds to a timer-setting step 292 which is the same as step 274. From step 292 a loop 294 is entered to repeat the portion of subroutine 262 commencing with step 276. Each time this portion of subroutine 262 is executed, another sample of the output of photodetector 32 is taken and converted by converter 169 into a digital signal or word which is stored in buffer 286. When all twenty-four readings are taken and stored to complete the sampling operation, the decision at step 290 becomes affirmative, thus completing the execution of subroutine 262 and returning at 296 to the run-in subroutine 256 (FIG. 23) Upon returning to subroutine 256, a step 297 is entered to call an X advance subroutine 298 (FIG. 26). Except for the direction in which the X-motion motor 74 is advanced, the X advance subroutine 298 is the same as the X home subroutine 220. Accordingly, like reference numerals have been used to designate like steps of the two subroutines except that the reference numerals used for subroutine 298 have been suffixed by the letter "b" to distinguish them from the reference numerals used for subroutine 230.

As shown in FIG. 26, the X advance step 232*a* differs from the X home subroutine 220 in that motor, instead of being advanced in the reverse direction, is now advanced in the forward direction to displace carriage 60 away from its home position for moving plate 48 towards the path of the photometer's light beam 146.

Upon executing the X advance subroutine 298 to commenc forward motion of carriage 60, operation is returned to the run-in routine 256 at step 349 where a Y advance subroutine 350 (FIG. 27) is called. Except for the direction in which the Y-motion motor 74*a* is advanced, the Y advance subroutine 350 is the same as the Y home subroutine 244. Accordingly, like reference characters have been used to designate like steps in the two subroutines except that the letter "c" has been substituted in the reference characters for subroutine 350 to distinghish them from the reference characters used for subroutine 244.

Figure 27:
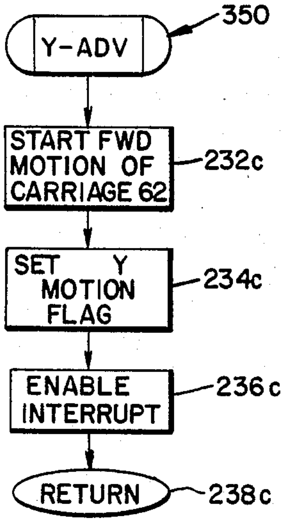
FIG. 27 ia a flow chart of the Y advance subroutine.

As shown in FIG. 27, the Y advance step 232*c* differ from the Y home subroutine 244 in that motor, instead of being advanced in the reversed direction, is now advanced in the forward direction to displace carriage 62 away from its home position for moving plate 48 towards the path of the photometer's light beam 146.

At this stage of the operation both carriages 60 and 62 are travelling forward in directions to advance the A1 well in plate 48 towards the photometer's light beam path 146. Following execution of the Y advance subroutine 350 operation is returned to the run-in routine 256 at step 351 to call a return subroutine 352 (FIG. 28).

Figure 28:
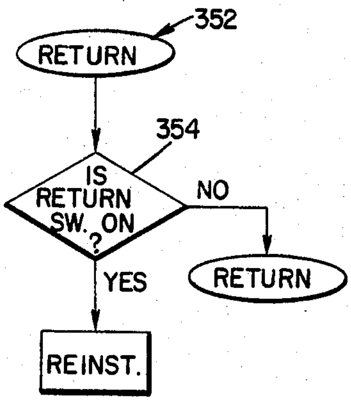
FIG. 28 is a flow chart of the return subroutine.

As shown in FIG. 28, the return subroutine 352 comprises a decision step 354 for checking the condition of a return switch 356 (see FIG. 1) on the front panel of the photometer. If return switch 356 is on, the operating sequence is reinstated to return carriages 60 and 62 to their home positions, thus aborting the reading operation. If the return switch is off, operation is returned to the run-in subroutine where a further decision step 358 is entered. Decision step 358 checks the X- and Y-motion flags to determine if there is motion of either one or both of the carriages 60 and 62. If either or both of the carriages 60 and 62 are still in motion a waiting loop 360 is entered.

When the X carriage 60 reaches a position where tooth 110 interrupts the light beam from source 123, sensor 104 transmits an interrupt signal to microprocessor 182. When the Y carriage 62 arrives at a position where tooth 136 interrupts the light beam from source 123*a*, sensor 104*a* transmits a similar interrupting signal to microprocessor 182. When both of these interrupting signals have been transmitted plate 48 will be at a position where the photometer's light beam 146 passes through the intersection between lines 148 and 150 (see FIG. 12). This point is also indicated at 360-1 in FIG. 13 and is immediately adjacent to the leading edge of the A1 well in plate 48 as previously explained.

Upon receiving the first interrupt signal (say the signal from sensor 104) microprocessor 182 calls and executes the interrupt routine 237. At this point the X-motion flag is set so that the decision at step 300 will be affirmative, thus entering step 304. At step 304 the decision is made that the motion of carriage 60 is forward, thus entering the input step 364 to check the signal status of sensor 104.

Following step 364 another decision step 366 is entered which looks at the input from sensor 104 to determine if carriage 60 has arrived at the position where tooth 110 interrupts the light beam from source 123. If the decision is negative step 302 is entered to check the Y-motion flag. If the decision at step 366 is affirmative, step 368 is entered to increment the X postition counter 312 and to reset or turn off the X-motion flag. Following step 368, an output step 370 is entered to disengage clutch 76 and apply brake 84 to stop the motion of carriage 60 at the position where the photometer's light beam 146 intersects the column line 148 (FIG. 12).

Following step 370 decision step 302 is entered to check the Y-motion flag, and if it is on, decision step 318 is entered. At this stage of the operation the motion of carriage 62 will be forward, thus entering another input step 372 to check the signal from sensor 104*a*.

If carriage 62 has arrived at the position where sensor 104*a* is transmitting its interrupt signal, the ensuing decision step 374 responds affirmatively with the result that step 376 is entered. If carriage 62 has not as yet reached the position where tooth 136 interrupts the light beam from source 126*a* the decision at step 374 will be negative, thus directing the operation to enter step 316. Assuming that the decision at step 374 is affirmative, step 376 is entered to increment the Y position counter and to reset the Y-motion flag. Following step 376, step 316 is entered to execute the remainder of the interrupt routine.

Upon the return from routine 237 to the run-in routine (FIG. 23), the decision at step 358 now becomes negative because both the X- and Y-motion flags have been reset, although the Y carriage 62 is still travelling in the forward direction. As a result of the negative decision at step 358, step 390 is entered to recall the read subroutine 262 while carriage 62 is still travelling in its forward direction where the movement of plate 48 is such that the photometer's light beam 146 traverses along line 148 diametrically across the A1 well in plate 48. Therefore, in this execution of the read subroutine 262 converter 169 will sample the analog output of photodetector 32 at points 360-1 through 360-24 as shown in FIG. 13.

In the computer's program, the A1 well in plate 48 has been preselected as the blanking well. Therefore no reagents, blood or other material are placed in the A1 well so that the twenty-four digital optical density measurements across the diameter of the well will be electrically processed to provide a blanking reference which indicates the optical density of the well's bottom. This blanking reference and the previously described air blank are substracted from the optical density readings made for the other wells in plate 48 to obtain accurate optical density readings of the materials in the other wells of plate 48.

Upon completing the twenty-four optical density readings at the A1 well in plate 48, the Y carriage motion continues without interruption, and the operation proceeds to a decision step 400 (FIG. 23) in the run-in routine to determine whether all eight wells in the plate's column of wells have been read. The count in counter 328 will indicate the number of wells thus far read in the columns. Since only the first well in column 1 has been read at this stage the decision is negative, thus entering step 402 to call the Y advance subroutine 350. Execution of the Y advance subroutine 350 at this stage sets the Y-motion flag and enables the microprocessor interrupt to recondition microprocessor 182 to recognize an interrupt signal from the sensor 104*a* and to execute the interrupt routine 237 upon reception of such interrupt. The execution of the Y advance subroutine at this stage is not required to recommence forward motion of carriage 62 because it already is in motion along line 148.

Following step 402, step 404 is entered to call and execute the return subroutine 352. Assuming that the return switch 356 is still off a decision step 406 is entered to check the X-motion and Y-motion flags for their set conditions. If either or both of the motion flags are set, a waiting loop 408 is entered until both flags are reset.

When carriage 62 arrives at a position where the tooth 137 of comb 103 interrupts the light beam from source 123*a*, sensor 104*a* transmits an interrupt signal to microprocessor 182, causing re-execution of the interrupt routine 257. Re-execution of routine 257 resets the Y-motion flag, but does not halt the forward movement of carriage 62 as previously explained. At this stage, the photometer's light beam 146 will be at the intersection of lines 148 and 151 (see FIG. 12), which is position 360-1 (FIG. 13) on the B1 well.

With both of the X- and Y-motion flags reset, the decision at step 406 will be negative, thus entering a further decision step 409 to determine if carriage 62 is at its home position. At this stage, carriage 62 will be away from its home position. The decision at step 409 is therefore negative causing the operation to enter a loop 410 to re-execute the portion of the run-in subroutine 256 commencing with step 390, which again calls the read subroutine 262 for producing and storing twenty-four optical density digital readings of the contents in the B1 well at equally spaced apart points diametrically across the well along column line 148 in the same manner described for the A1 well. The operation remains in loop 410 repeating itself for each of the remaining wells in column 1 of plate 48.

Upon performing the read subroutine 262 for the last well in column 1 (that is, the H1 well) plate 48 will have been advanced by carriage 62 to a position where the photometer's light beam 146 passes through the last of the twenty-four reading points 360-24 (FIG. 13). At this stage, the count stored in the Y position counter 328 will be eight, indicating that all eight wells in column have been read. Therefore, the decision at step 400 will be affirmative to enter a step 420 for calling the Y home subroutine 244. Execution of the Y home subroutine reverses the operation of motor 74*a*, thus reversing the motion of carriage 62 to commence advancement of carriage 62 towards its home position along line 148 (FIG. 12). When carriage 62 arrives at its home position the last tooth 433 on comb 130 interrupts the light beam from source 126*a*. Sensor 106*a* therefore transmits its interrupt signal to microprocessor 182. In response to this interrupt, microprocessor 182 executes the previously described interrupt service routine 237. As a result, the Y-motion flag will be reset or turned off.

Figure 29:
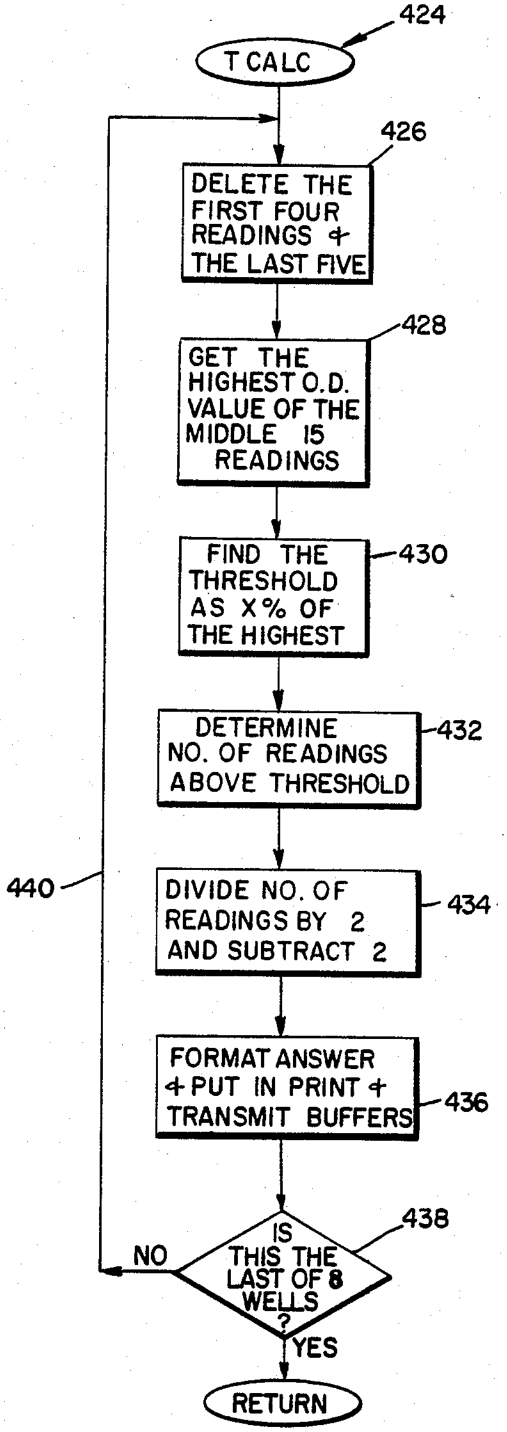
FIG. 29 ia a flow chart for the Tcalc subroutine.

While carriage 62 is being advanced towards its home position a further step 422 is entered to call a Tcalc subroutine 424 (FIG. 29). For each set of the twenty-four optical density measurements for each well in plate 48, the Tcalc subroutine 424 computes a suitable numerical value such as the previously described value ranging from 1 to 5.5 to indicate the size of the agglutination button or other solid mass in the bottom of the well and also to indicate the extent or nature of the reaction as in the case, for example, of the previously described hemagglutination inhibition reaction or assay.

As shown in FIG. 29, subroutine 424 commences with a step 426 where the first four and the last five of the twenty-four stored optical density measurements are deleted. Following step 426 a further step 428 is entered to determine which of the remaining optical density measurements has the highest optical density value. Thereafter, a step 430 is entered to establish a threshold as a preselected percentage of the highest optical density value, which highest value was determined in step 428. Such percentage may, for example, be 70% of the highest optical density value. Thereafter, step 432 is entered to identify and count the number of optical density measurements having values greater than the above mentioned threshold.

Following step 432, step 434 is entered in which the number of optical density measurements above the threshold is divided by two, and the quotient is reduced by a preselected number such as two to produce an answer equal to the quotient minus two. In step 436 the answer is formatted and may be placed in a print buffer (not shown) for readout and/or a transmit buffer (not shown) for tranmission to computer 210 for further processing.

After formatting the answer, a decision step 438 is entered to determine if answers for all eight wells in the column just scanned have been computed. If not, the operation enters a loop 440 to repeat execution of the subroutine 424 until the answers for all eight wells are obtained and stored in RAM 186, at which time the decision at step 438 becomes affirmative to return operation to the run-in routine 256.

Referring back to FIG. 23, the operation next enters a step 442 for calling a print subroutine (not shown) and/or a data transmit subroutine (also not shown). Each of these subroutines may be of any suitable type.

The print subroutine operates printer 180 to provide a print-out for each well 50 in the scanned column of wells. The print-out for each well includes the well's designation (e.g., A1, B1, etc.) and its associated answer (the computed reading) obtained by execution of subroutine 424. The transmit subroutine provides for the transmission of the computed answers and/or the raw data (the individual sets of twenty-four optical density measurments for each well) to computer 210 or other equipment for further processing. Additionally, another subroutine may be used to read out the answers and their associated well designations on display 178, which may be of the LED type. Display 178 may also be operated to read out the X-Y coordinate position of plate 48 relative to beam 146 in terms of the microtest plate well designations (e.g., A1, B1, etc.) while the scanning and optical density reading operation is in progress.

Following step 442, a decision step 444 is entered to check or interrogate the Y-motion flag to determine if carriage 62 is still in the process of returning to its home position. If movement of carriage is still in progress a waiting loop 446 is entered.

When carriage 62 arrives at its home position the Y-motion flag will be reset as previously noted, and the decision at step 444 therefore becomes negative, thus entering the next decision step 448 which determines whether or not the present position of carriage 60 is the last position in the X direction, that is, the plate position where the column line 450 (see FIG. 12) perpendicularly intersecting the longitudinal axes of the wells in column 12 intersects the photometer's light beam 146. In essence, this decision step determines whether all of the wells 50 in plate 48 have been read.

At the present stage of the operation, only the wells in column 1 have been read thus placing a count of 1 in the X position counter 312. Step 448 therefore interrogates the X position counter and if the count is not 12, the decision is negative to enter a further step 452 for calling the X advance subroutine 298.

Execution of the X advance subroutine imparts motion to carriage 60 in the forward direction to move over to column 2 in plate 48 while the Y carriage 62 is still at its home position.

Upon moving plate 48 to a position where the column line 149 (FIG. 12) intersects the photometer's light beam 146, the tooth 111 on comb 102 interrupts the light beam from source 123 causing sensor 104 to transmit its interrupt signal to microprocessor 182. As a result, the interrupt routine 237 will be executed again, stopping further forward advancement of the X carriage 60. The system is now ready for reading the wells in column 2.

Following step 452, (FIG. 23) step 404 is re-entered and if the return switch is still off, the X- and Y-motion flags are checked at step 406 as previously described. Assuming that both flags have been reset, decision step 409 is re-entered. At this stage, carriage 62 is at its home position resulting in an affirmative decision to proceed to step 455 for again calling the Y advance subroutine 350 and thus commencing the forward motion of carriage 62 for scanning and reading the wells in column 2 similar to the operation previously described for column 1.

When all eight of the wells 50 in the plate's column 2 have been read, carriage 62 is returned to its home position, and carriage 60 is advanced in the forward direction to column 3 to repeat the scanning and reading operation for the wells in column 3. Thus, the foregoing operation is repeated for each of the remaining columns in plate 48. When the wells in column 12 have been scanned and read, a count of 12 will be present in the X position counter 312. As a result, the decision at step 448 now becomes affirmative to proceed to step 457 where the X home subroutine 220 is called for returning carriage 60 to its home position. Because of the interrupt produced by returning carriages 60 and 62 to their home positions, the X- and Y-motion flags will at this time be reset. As a result, a negative decision will be made at step 458 to proceed to step 460 for turning off the run light and returning the operation to the main program at step 248 (FIG. 20) in preparation for another run.

From the foregoing description it will be appreciated that the scanning motion for reading the optical densities of the contents in wells 50 is continuous. This type of operation is advantageous over the type of operation in which motion is temporarily halted while making each optical density measurement because the latter type of operation tends to unsettle the agglutination button or other particulate material in the bottom of the well, thus requiring a resettling time in order to achieve accurate measurements.

It is evident that one or more programming steps may be involved in the actual implementation of the various steps described for the illustrated flow chart. Since programming of such steps is well within the skill of an average programmer, a complete program listing is not included herein.

For the standard type of microtitration plate shown in the drawings, the digital readings or conversions made by converter 169 will be at ponts which are uniformly spaced apart from one another by 0.01 inch diametrically across the well (that is, along a line extending diametrically of the well and therefore prependicularly intersecting the well's longitudinal axis.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An apparatus for determining the presence or absence, size and pattern of an agglutination button or other solid mass in the bottom of a microtest well or other sample-holding vessel comprising first means for measuring the optical density of the contents of a microtest well or other sample-holding vessel, and second means for electrically processing the optical density measurements made by the first means for determining a certain characteristic of said button or other mass, said first means comprising means providing a light beam, with a discrete focal point adapted to be focused on the contents of the well or other structure, means for causing said beam to scan across said well or other sample-holding vessel by moving said beam and well relative to each other, and a photodetector for sensing the energy level of the beam after it passes through the contents of the well or other sample vessel to produce an output signal which is proportional to the transmittance of the contents in the well or other sample-holding vessel as the beam moves relative to the well or other sample-holding vessel, and said second means being electrically connected to said photodetector for electrically processing said output signal by sampling said signal at a plurality of mutually spaced points diametrically across the well or other vessel to produce an output signal proportional to the transmittance at each of said points and by analyzing said signals to determine the change in optical density across the well or other vessel as a measure of the presence and size of an agglutination button or other solid mass in the bottom of a well or other vessel.

2. The apparatus of claim 1 wherein said first means produces an analog output signal.

3. The apparatus of claim 2 wherein said second means produces a digital output signal proportional to the transmittance at each of said points from the sampled analog output signals from said first means.

4. The apparatus of claim 1 wherein said second means includes sampling means for sampling the first means output signal at mutually spaced discrete points about 0.01 inches apart across the well or other vessel.

5. The apparatus of claim 1 wherein said second means includes sampling means for sampling the first means output signal at least at 24 discrete points diametrically across the well or other vessel.

6. The apparatus of claim 1 wherein the second means includes means for computing the optical density at each of the points wherein the signal is sampled.

7. The apparatus of claim 6 wherein said means for computing includes blanking means for determining the optical density of the ambient air and bottom of the well or other vessel and means for correcting the computed optical density to compensate for said densities.

8. A method for determining the presence or absence, size and pattern of an agglutination button or other solid mass in the bottom of a microtest well or other sample-holding vessel comprising the steps of:

providing a light beam having a discrete focal point adapted to be focused on the contents of the well or other vessel and a photodetector therefor;

directing said light beam through said well or other vessel and the contents thereof;

moving said well or other vessel and said beam and detector relative to each other such that said beam scans diametrically across said well or other vessel;

producing an output signal from the detector proportional to the light absorbance of said beam as it passes through the well or other vessel and contents thereof;

sampling said signal at each of a plurality of discrete points spaced across the diameter of the well or other vessel; and determining the change in optical density, from said signals, across the well or other vessel to compute the presence or absence, size and pattern of an agglutination button or other solid mass in the well or other vessel.

9. The method of claim 8 wherein the step of determining the change in optical density includes the steps of measuring the light absorbance of the ambient air and the bottom of said well or other vessel and correcting each output signal therefor so that said signal will be proportional to the optical density of the contents of said well or other vessel.

10. The method of claim 8 wherein the step of sampling said signal includes the step of sampling said signal at points spaced about 0.01 inches apart across the well or other vessel.

11. The method of claim 8 wherein the step of sampling further comprises sampling said signal at least 24 times at equidistantly spaced points across the well or other vessel.

12. The method of claim 8 wherein the step of producing an output signal further comprises producing an analog output signal.

13. The method of claim 12 further comprising converting each signal sample to a digital output signal proportional to the optical density at each of said points.

* * * * *